United States Patent [19]
Eaton et al.

[11] Patent Number: 4,622,462
[45] Date of Patent: * Nov. 11, 1986

[54] METHOD AND APPARATUS FOR THREE-DIMENSIONAL SCANNING

[75] Inventors: Homer L. Eaton; John D. Shaylor-Billings, both of Leucadia, Calif.

[73] Assignee: MTS Vektronics Corporation, Carlsbad, Calif.

[*] Notice: The portion of the term of this patent subsequent to Oct. 2, 2001 has been disclaimed.

[21] Appl. No.: 477,744

[22] Filed: Mar. 23, 1983

Related U.S. Application Data

[63] Continuation-in-part of Ser. No. 383,950, Jun. 1, 1982, Pat. No. 4,475,035, which is a continuation-in-part of Ser. No. 272,757, Jun. 11, 1981, abandoned.

[51] Int. Cl.$^4$ ............................................. H01J 3/14
[52] U.S. Cl. .................................... 250/236; 356/376
[58] Field of Search .............. 250/234, 235, 236, 230, 250/560; 356/376, 1; 350/6.4, 6.5

[56] References Cited

U.S. PATENT DOCUMENTS

| | | | |
|---|---|---|---|
| 3,700,903 | 10/1972 | Adler et al. | 250/217 |
| 3,782,827 | 1/1974 | Nisenson et al. | 356/120 |
| 3,807,870 | 4/1974 | Kalman | 356/161 |
| 3,866,038 | 2/1975 | Korth | 250/236 |
| 3,874,798 | 4/1975 | Antonsson et al. | 356/159 |
| 3,975,102 | 8/1976 | Rosenfeld et al. | 356/167 |
| 4,146,926 | 3/1979 | Clerget et al. | 364/556 |
| 4,158,507 | 6/1979 | Himmel | 356/376 |
| 4,171,917 | 10/1979 | Pirlet | 356/376 |
| 4,204,772 | 5/1980 | Balasubramanian | 356/376 |
| 4,290,698 | 9/1981 | Milana | 356/371 |
| 4,322,627 | 12/1979 | Pirlet | 250/561 |
| 4,339,644 | 7/1982 | Wiklund | 250/577 |
| 4,349,274 | 9/1982 | Steele | 356/1 |
| 4,440,496 | 4/1984 | Milana | 356/241 |
| 4,475,035 | 10/1982 | Eaton et al. | 250/236 |

FOREIGN PATENT DOCUMENTS 1405331 1/1973 United Kingdom .

OTHER PUBLICATIONS

Paper entitled "An Overview of Electro-Optical Inspection", by T. R. Pryor, Diffracto Limited, Windsor, Ontario, Canada, Figure 5.

*Primary Examiner*—Davis L. Willis
*Assistant Examiner*—James G. Gatto
*Attorney, Agent, or Firm*—Gausewitz, Carr & Rothenberg

[57] ABSTRACT

Three-dimensional information and a three-dimensional display of the surface of an object is provided by a scanning laser beam mounted on a high-speed rotating disc to repetitively scan across an object transported below the disc upon a moving carrier. Light reflected from the object surface back along the axis of the scanning beam is detected to indicate surface characteristics, such as reflection intensity. Positions of the projected beam in the course of its scanning rotation and of the carrier in the course of its transport motion are detected to generate signals that define the XY position of the scanning beam. Light of the projected energy beam, as reflected from the object at an angle to the beam axis, is imaged by a second lens upon a linear detector array, whereby the position of the image along the linear detector array will indicate elevation of the reflecting area along the axis of the projected beam. The signals defining the XY position of the scanning beam also define the XY positions of the elevation data from the linear array and the XY positions of the information obtained from the detector of coaxially reflected energy. Several solid-state lasers and detectors are carried by the rotating disc in one embodiment to provide measurements of different object characteristics and to improve scan speed or resolution.

25 Claims, 9 Drawing Figures

METHOD AND APPARATUS FOR THREE-DIMENSIONAL SCANNING

This application is a continuation-in-part of U.S. patent application Ser. No. 383,950, filed June 1, 1982, now U.S. Pat. No. 4,475,035, for METHOD AND APPARATUS FOR SCANNING, which, in turn, is a continuation-in-part of U.S. patent application Ser. No. 272,757, filed June 11, 1981, now abandoned, for METHOD AND APPARATUS FOR SCANNING. Disclosures of both of the prior applications are incorporated by this reference as though fully set forth herein.

BACKGROUND OF THE INVENTION

The present invention relates to surface scanning of parts and more particularly concerns improved scanning methods and apparatus to provide precise information concerning one or more of surface characteristics, configuration, orientation, discontinuity, and elevation, and provides detailed three-dimensional data of an object surface.

Our prior application describes scanning apparatus that identifies parts and measures surface detail by sensing intensity of light reflected from the part surface back along the axis of a rotating scanning beam that is directed to the part in a perpendicular scanning pattern. A scanning laser beam is projected from a rapidly spinning disc to a part mounted on a conveyor which moves the part across and through the circular scan pattern of the rotating beam. Thus, the beam traverses the part many times during one passage of the conveyor along a number of closely-spaced scan paths that cover the entire part surface. By sensing the beam position at one or more points in its circular scan and by sensing the conveyor position, a set of signals are generated that define the XY coordinates of the beam position at each of a number of points determined by a high frequency clock and the speed of beam rotation and conveyor travel. Correlating the timing of reflection intensity signals from the detector with the beam scan position signals provides data defining reflection intensity of the scanned object surface at each of a number of very closely-spaced points on the object surface. In effect, a two-dimensional picture of the object has been made and, in fact, can be displayed as such on a video screen.

A great deal of valuable information is rapidly and efficiently obtained with great precision with the use of the apparatus described in our prior application. Nevertheless, for many applications, including inspection and measurement, it is desirable to obtain elevation information in addition to the two-dimensional information previously obtainable.

Our prior application contemplates obtaining elevational information on the part by replacing the scanning laser with a laser distance measuring system employing interferometry and Droppler techniques. However, such a system is large, complex, expensive and difficult to mount on a rapidly spinning disc.

Optical triangulation techniques have been employed to determine elevation, but these have been static-type arrangements or used in systems that can be moved for measurement from one point to another only in limited fashions and at low speed. No such arrangements have been suggested for complete elevation mapping of an object surface.

Resolution of the information (e.g., the number and spacing of data points) provided by the apparatus of our prior invention depends in part on scanning speed, which is limited by physical limits on the speed of rotation of discs of a useful size. Time required for an entire scan will vary with required resolution and the limited scanning speed. Therefore, a trade-off between resolution and overall scan time may be required, although in many instances it is desired to maximize resolution and minimize scan time.

Accordingly, it is an object of the present invention to avoid the limitations of prior apparatus, to provide two-dimensional scanning of increased speed and resolution, and, in addition, to provide elevation information.

SUMMARY OF THE INVENTION

In carrying out principles of the present invention in accordance with a preferred embodiment thereof, three-dimensional scanning is achieved by moving a scanning energy beam in a scan pattern across an object to successively illuminate small areas of the object, generating position signals defining positions in a plane of a plurality of the illuminated areas, moving a scanning receiver across the object in synchronism with the energy beam to receive energy reflected from the illuminated areas at an angle to a normal to said plane, and generating from the reflected energy received by the receiver elevation signals that define relative elevations of the illuminated areas. The apparatus, according to the invention, includes a movably mounted support, means for effecting relative scanning motion of the support and an object to be scanned, means for projecting an energy beam from the support along a beam axis directed to an object to be scanned, the beam having a scanned motion relative to the object, first and second mutually spaced receivers mounted to the support for motion therewith relative to the object to be scanned, and means for moving the object relative to the pattern produced by the path of the scanning motion.

According to another feature of the invention, a plurality of parallel, synchronous scanning beams are caused to scan the object in unison, thereby to increase the scanning speed and/or the resolution available.

DETAILED DESCRIPTION OF THE INVENTION

Figure 1:
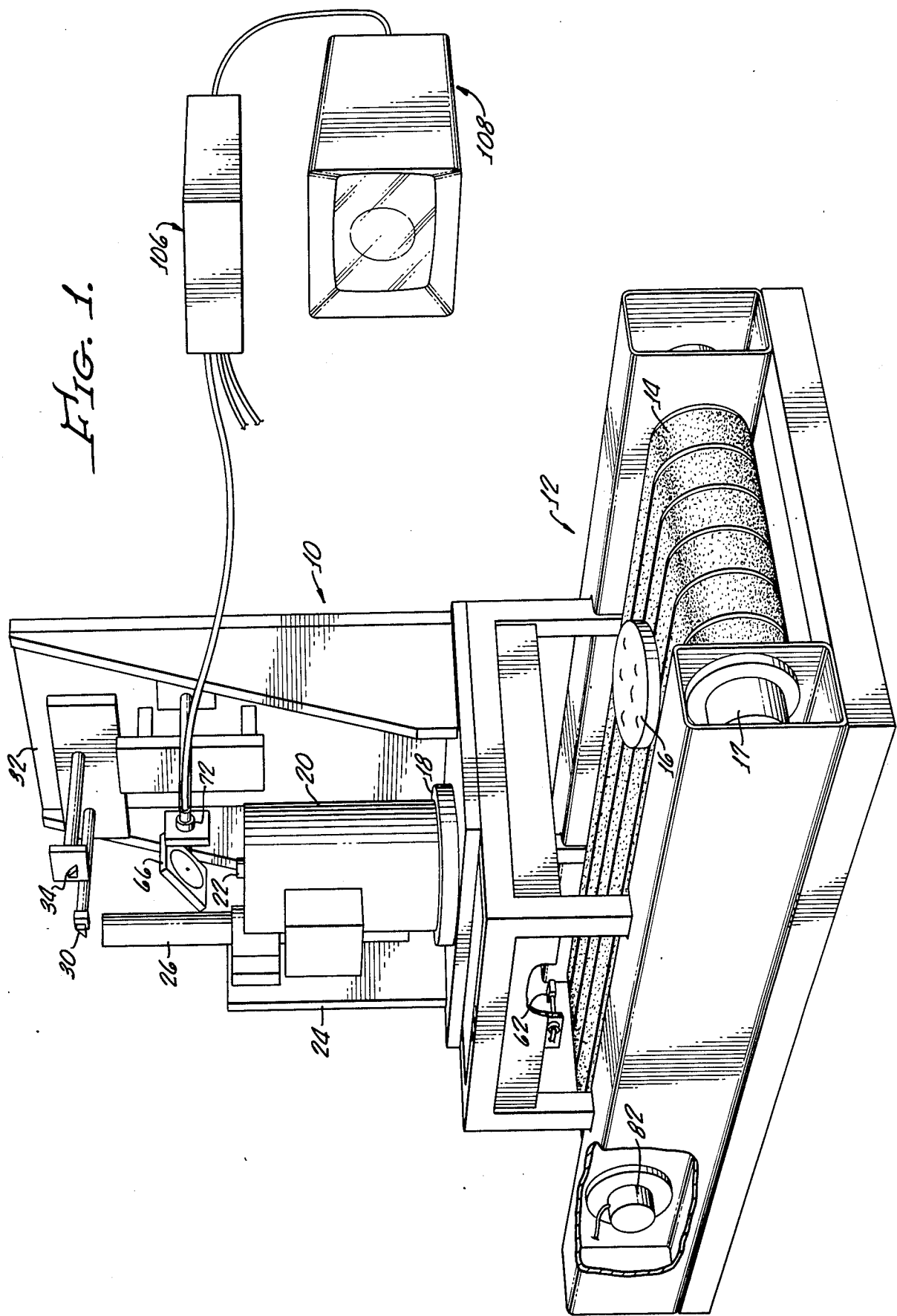
FIG. 1 is a pictorial illustration of scanning apparatus embodying principles of the present invention.
Figure 2:
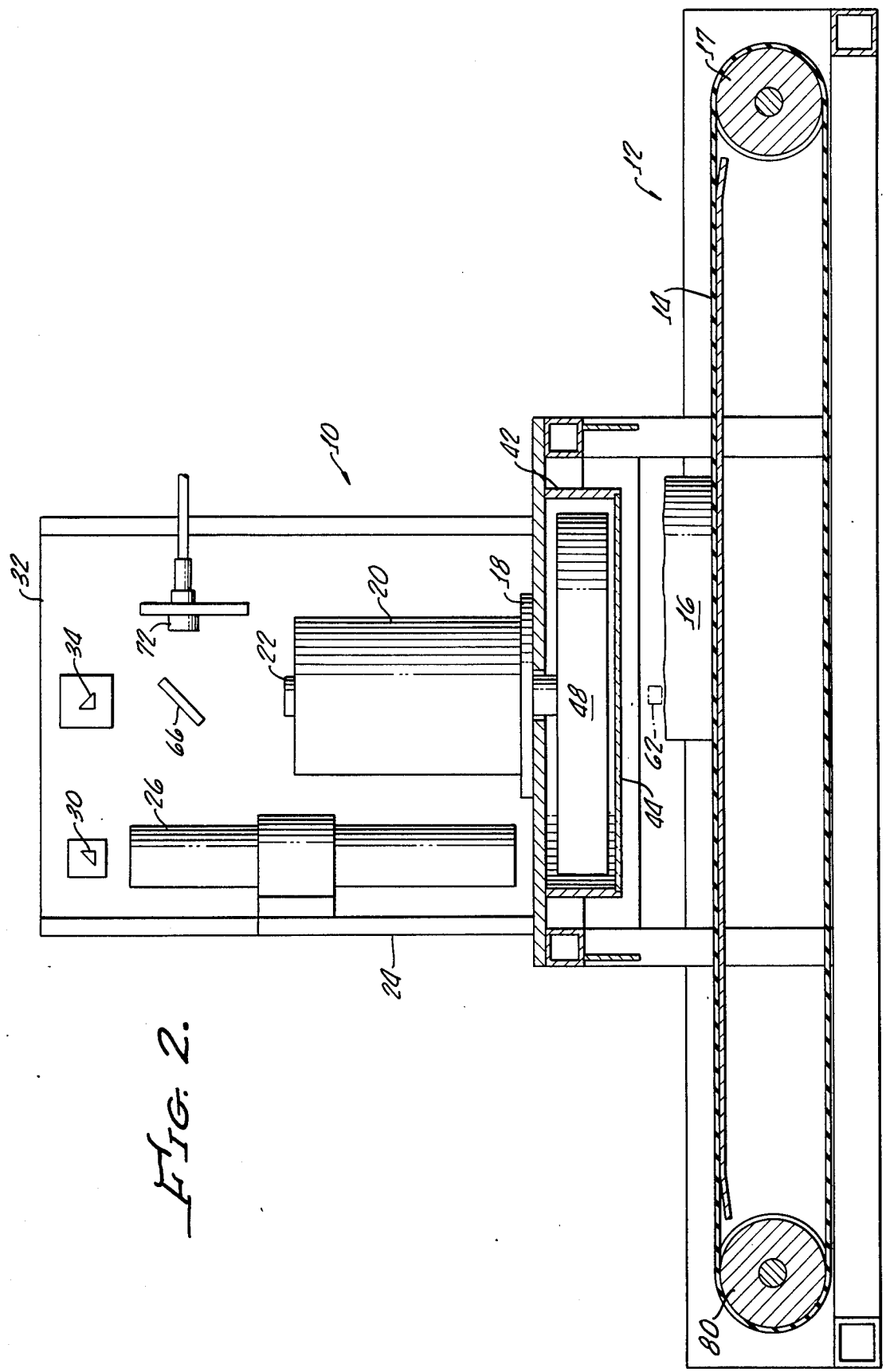
FIG. 2 is a side elevation of the apparatus of FIG. 1.

As illustrated in FIG. 1, a scanner embodying principles of the present invention comprises a support structure 10 fixedly supported above and adjacent to a conveyor 12 having a movable belt 14 on which is placed an object 16 that is to be scanned. The object to be scanned can be of many different sizes, shapes and construction, being illustrated as a generally circular object with an uneven surface. The conveyor is driven by a motor 17 to move the belt and the object from the left to right as viewed in FIG. 1, close to and directly beneath the scanning apparatus, and entirely across the scan pattern thereof.

Figure 3:
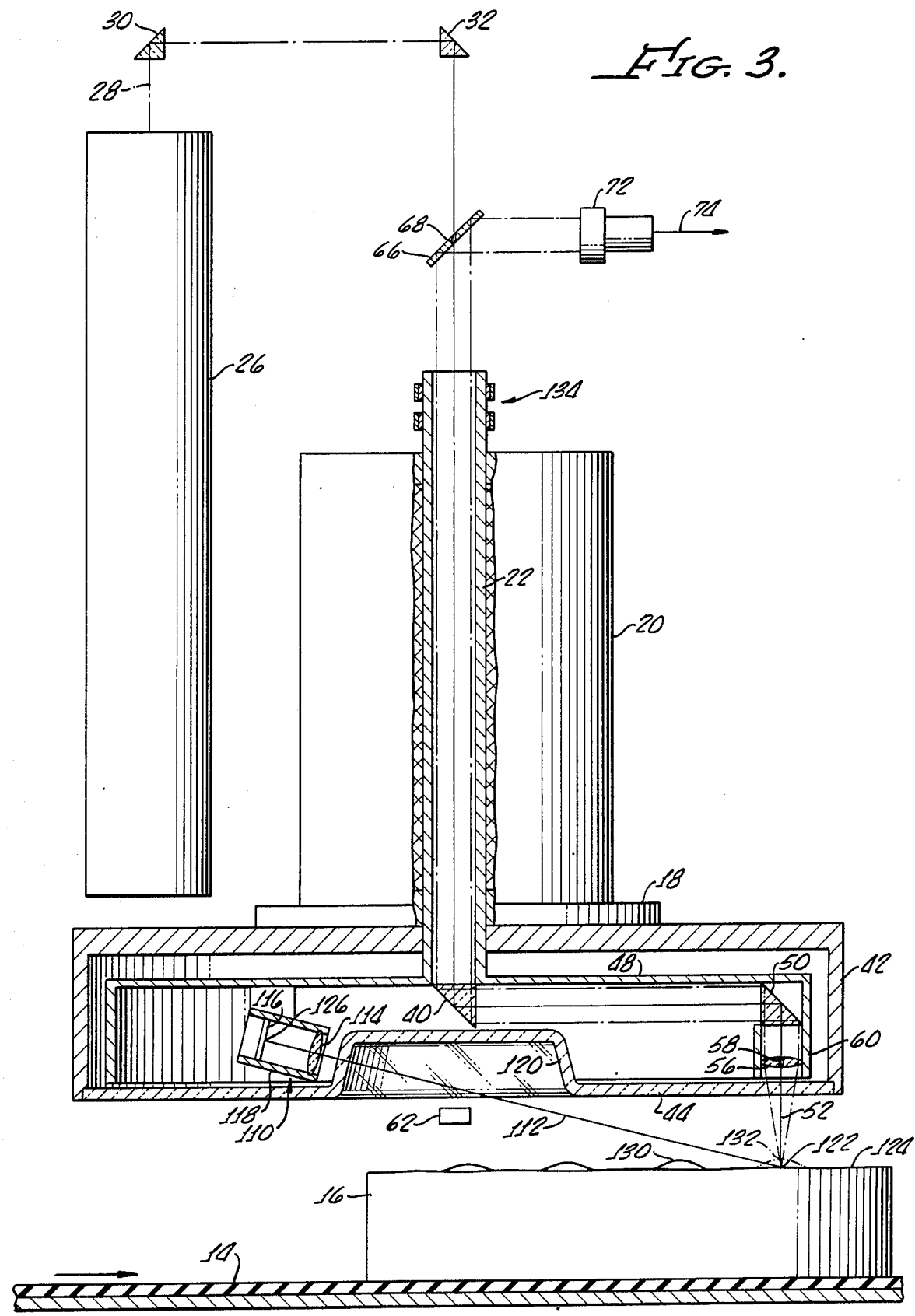
FIG. 3 is a simplified elevational section of the apparatus of FIG. 1.

The support structure comprises a rigid base 18 on which is fixedly mounted a motor 20 having a hollow vertical shaft 22 that is rotated at high speed by the motor. Fixedly mounted to an upstanding sidewall 24 is an energy beam generator in the form of a laser 26 that generates and projects a very small cross-sectional area light beam 28 (FIG. 3) to a first 90° reflecting prism 30 mounted at the upper end of an upstanding rear wall 32 of structure 10. Prism 30 turns the light beam through 90° to a second 90° reflecting prism 34, also fixed to the upper end of wall 32, and positioned in alignment with the center of the hollow motor shaft, whereby the beam is reflected downwardly through the center of the shaft 22. At the bottom of the shaft is mounted a third 90° reflecting prism 40 (FIG. 3) which again turns the light beam at an angle of 90° so that the beam is now directed perpendicular to the axis of rotation of the motor shaft.

The scanner support structure includes an enlarged lower section 42 of generally inverted dish-shaped configuration having a downwardly facing end closed and sealed by a high-strength, rigid protective plate 44. Plate 44 is preferably made of a completely transparent material but may be made of any suitable opaque material, provided that transparent areas are provided for passing light in the optical paths to be described below.

Fixedly connected to the end of the hollow motor shaft 22 is a rotatable arm in the form of a disc 48 in the radially outer end of which is mounted a fourth 90° reflecting prism 50, positioned to receive the light beam from prism 40 and turn it through 90° along the path indicated by reference character 52. Accordingly, as the motor shaft is rotated, prisms 40 and 50 and disc 48 rotate about the shaft axis, causing the projected laser beam 52 to scan in a right circular cylindrical pattern centered on the axis of rotation of the scanner and having a radius equal to the radial displacement of the reflective prism 50 from the shaft axis. The arrangement provides an orthogonal scan, with the scanning beam always exiting parallel to the rotation axis and normal to the part supporting surface of conveyor belt 14. The interior of support structure lower section 42 may be evacuated to facilitate high speed rotation of disc 48.

A lens 56 having an axial hole 58 extending completely therethrough is fixedly mounted in a support 60 that is fixed to the end of rotating disc 48. The lens and its hole are coaxial with the projected beam 52 which passes freely through the lens. The lens is focused on the point of impingement of the beam upon the object being scanned.

A reference generator in the form of a light sensitive diode or equivalent 62 is fixed to the bottom of plate 44 in the path of the projected beam 52 so as to be illuminated momentarily by the beam during each cycle of its rotation.

Light projected from the rotating energy beam 52 is reflected from a very small area of the object upon which the beam impinges, and some of this reflected light is collected by the lens 56 which collimates the collected light and transmits it back to the reflecting prism 50. The collimated retroreflected light is then retro-directed along several legs of the outgoing laser beam path, from the prism 50 back to prism 40 and then upwardly along and through the hollow motor shaft. However, between the upper end of the motor shaft and the reflecting prism 34 there is mounted a 90° turning mirror 66 that has a central aperture 68 through which the outgoing laser beam passes without disturbance. The small hole 68 in the reflector 66 does not significantly affect the reflection by this mirror of the received collimated reflected energy which is directed to a detector 72 that provides an output signal on lead 74 having a magnitude directly related to the intensity of the light received thereby.

The belt 14 of conveyor 12 is entrained over a second roller 80 at the end opposite the motor, and a conveyor position detector 82, such as a conventional incremental shaft encoder, is mounted to the roller so as to provide from the detector encoder 82 a series of pulses, each of which denotes an increment of rotation of the roller and thus an increment of motion of the conveyor belt 14.

The laser beam moves in a cylindrical scan pattern and scans a circular path that crosses the part 16 as the latter moves relative to the scan path. As the part 16 moves across the scan path of the laser beam, the latter makes many passes across the part. The part is initially scanned repetitively by one side of the scan path and then it is scanned repetitively by the other side of the scan pattern as the conveyor carries the part completely across the circular scan path.

From the pulse trains provided at the outputs of reference detector 62 and conveyor position encoder 82, the position of the area of the part illuminated by the beam at each of a large number of points in its scan is determined. Geometry and equations for identifying beam position are described in detail in above mentioned applications U.S. Ser. No. 383,950 now U.S. Pat. No. 4,475,035 and Ser. No. 272,757. As described in those applications, a clock signal is employed to read out signals identifying position coordinates at selected fixed time intervals.

The structure described to this point is the same as that described in the earlier applications identified above. The signals from the intensity detector 72, the beam position encoder 62, and the conveyor liner displacement detector 82 collectively define intensity of light reflected from a large number of points on the object and also define the relative positions of such points, thus enabling the making of a plot of intensity over the area of the object. The signals are fed to a data processor 106 which may digitize and store the intensity signals together with the position coordinate information, which then may be compared to similar stored intensity and position signals that have been previously generated on a scan of a part of known configuration. Such a comparison may indicate correspondence of the newly scanned part with the reference part. Alternatively or in addition, the stored information, representing intensity and coordinate position, may be fed to an oscilloscope 108 to provide a visual display of the scanned object.

In an exemplary embodiment, the disc rotates at 1,800 revolutions per minute and the conveyor travels at 1.25 inches per second so that the part advances approximately 0.042 inches during each beam rotation. However, as mentioned previously, the part is scanned twice, once by the left segment of the circular beam as the part enters the scan and a second time by the right segment of the beam scan pattern as the part leaves the scan, thus improving resolution. Other arrangements for still greater improvements of resolution will be described below.

In order to obtain elevation information for each of the coordinate points at which the laser beam position is, in effect, sampled by the system clock, a second or elevation receiver 110 (FIG. 3) is fixedly mounted to the disc 48 at a position spaced from the axis of the projected laser beam 52 (e.g., spaced from the path of the projected beam which passes through bus 56). The elevation receiver has a receiving axis that is inclined to the axis of beam 52 and also inclined to the direction of motion of the conveyor and object, the receiver axis being denoted at 112. The elevation receiver comprises a lens 114 and a linear array 116 of light detectors mounted in a housing 118 that is fixedly carried by the disc 48 and oriented to provided the receiver axis 112. Preferably, the plate 44 has a circular recess 120 with sides oriented perpendicular to axis 112 so as to minimize reflections from plate 44.

Axis 112 is directed to intersect the axis of the projected laser beam 52 at a point 122 that lies midway between the extremes of expected elevation of the surface 124 of part 16. If the part surface area illuminated by beam 52 is precisely at the nominal elevation 22, the image of the illuminated area at elevation 122 is focused by the receiver lens 114 at a point such as midpoint 126 on the linear array. If the part has a surface elevation variation, such as protrusions indicated at 130, the area illuminated by the beam is at a higher elevation 132, which has a different position along the beam axis 52 than does the area 122. In such a case, the image of the illuminated area at elevation 132 will be focused by lens 114 upon a point on the array 116 that is displaced from the point 126. The displacement of such image from the point 126 is directly related to the distance between points 122 and points 132 along the beam axis, and the direction of displacement depends on the sense of the elevation deviation, e.g., whether the area is higher or lower than nominal. Thus, the outputs of the detector array 116 define elevations of the areas illuminated by the scanning beam. By scanning each of the elements of the linear detector array 116 or by reading all of the elements in parallel and identifying the element or elements that receive the image from lens 114, the elevation of the area on the part that is illuminated by beam 52 is determined. Suitable circuitry (not shown) is carried by the rotating disc and connected for readout of the elevation information from linear array 116. Power is fed to such circuitry and the elevation data signals from such circuitry is fed to data processor 106 via slip rings 134 (FIG. 3) mounted to the motor shaft 22.

Thus, elevation receiver 110 scans the part in synchronism with the scanning beam 52 and is directed at the area of the part illuminated by the beam to thereby receive light reflected from the illuminated areas at an angle to the beam 52. The latter is always perpendicular to the plane of motion of the object as it is carried by the conveyor. Just as the reflected light intensity signals provided by detector 72 are coordinated with the beam scan position signals to thereby identify and/or enable display of surface reflection intensity at each of the computed XY coordinate positions on the part, so too the elevation signals provided from the linear array 116 are coordinated with the XY position signals of the beam. The same XY position signals produced at clocked positions of the scanning beam (as described in the above identified co-pending patent applications) also identify XY positions of illuminated areas of which the elevation is defined by the elevation signals that occur at the clocked sampling times. Accordingly, the apparatus provides data that defines a three-dimensional picture of the object surface. The reflected light intensity data provides a picture of the object surface according to reflection intensity in an XY plane that is normal to the axis of beam 52. The elevation signals from the array 116 provide elevation data for each of the XY coordinate positions that are sampled or defined by the clock interval. In effect, the described apparatus is a three-dimensional camera, simultaneously providing both a two-dimensional picture of the object surface and coordinated elevation data for each of the points at which surface reflection intensity is measured. Surprisingly and unexpectedly, merely by mounting the additional inclined axis elevation receiver 110 on the rotatable disc 48 allows the apparatus to add precision elevation detail, with high resolution, to the two-dimensional surface reflectivity information, and thus provides a three-dimensional camera. Because of the high-speed rotation of the disc and the high repetition rate of the sampling by the system clock pulses, the system does not merely provide an elevation measurement at a few preselected points on the surface of the object, but makes its measurements so rapidly and at so many points in its scanning path as to provide a true three-dimensional, high resolution picture of the entire surface of the object being scanned. Resolution can be increased by decreasing conveyor and scan beam rotation speed, but at the cost of increased total time of scan.

Figure 4:
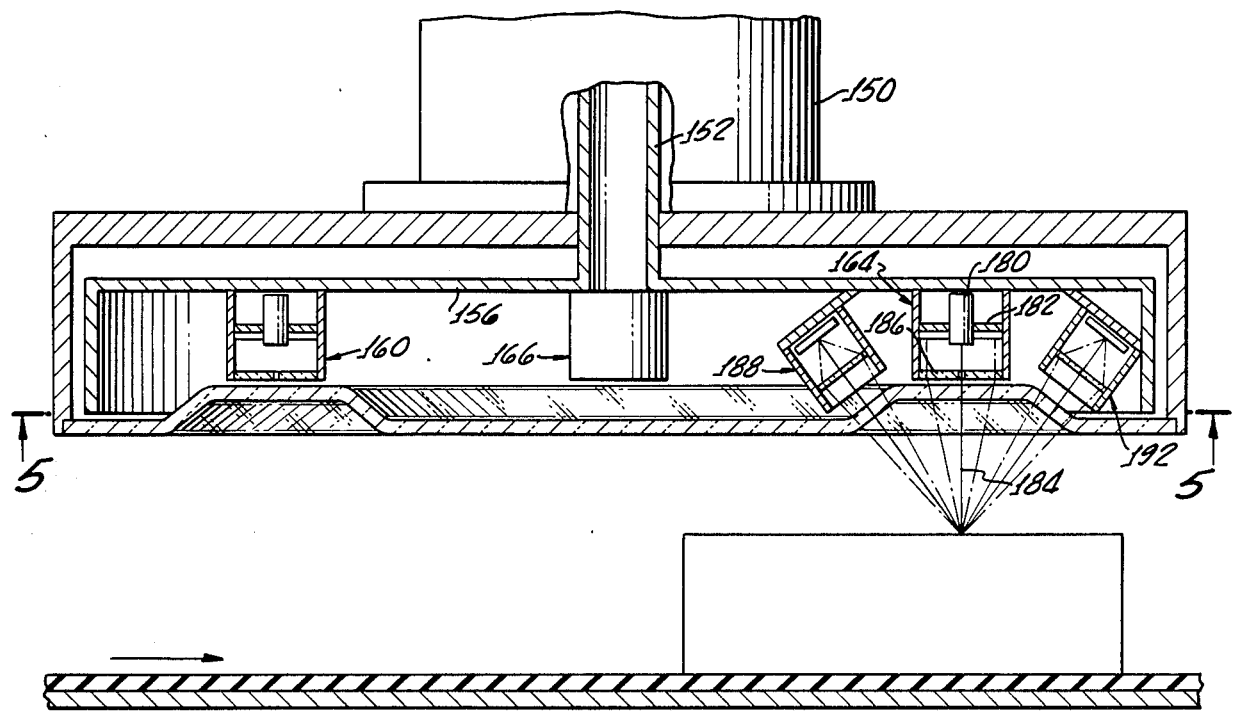
FIGS. 4 and 5 illustrate a modification of the apparatus of FIG. 1.
Figure 5:
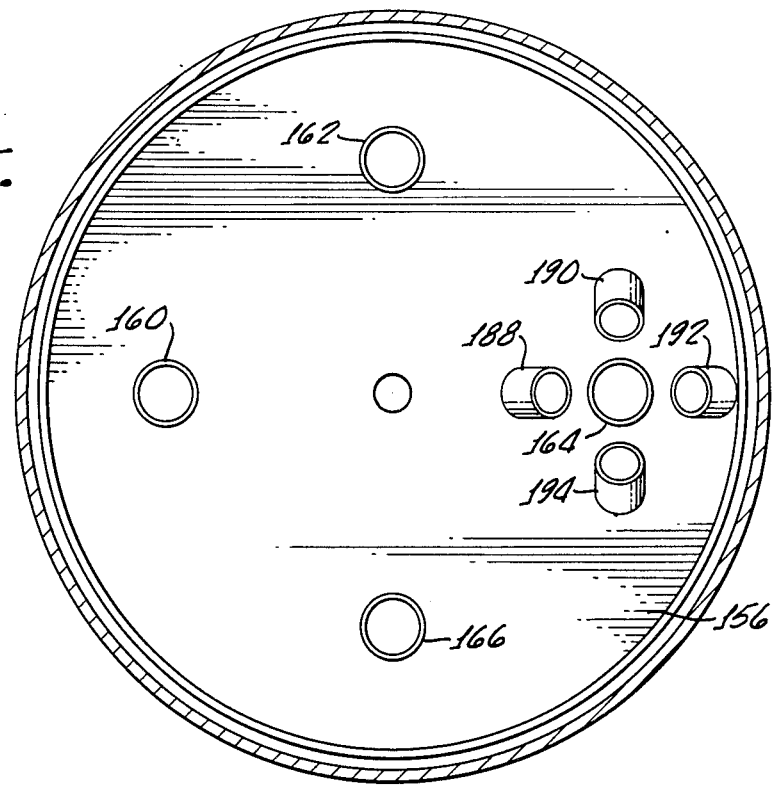

To decrease the total time required for scan of a part or to further increase resolution, or both, the apparatus may be modified to provide a plurality of spaced and mutually parallel scanning beams, each of which may have its own coaxial receiver. Any one or more of such beams may cooperate with a plurality of such inclined axis elevation receivers surrounding the projected perpendicular beam and all directed at the area illuminated thereby. Such an arrangement is illustrated in FIGS. 4 and 5 which shows a motor 150 driving a shaft 152 on which are mounted slip rings (not shown) and which is connected to drive a rotatable disc 156 at a high rotational speed. Disc 156 fixedly carries a plurality of solid-state laser receiver combinations 160, 162, 164 and 166 of the type illustrated in FIGS. 8 and 9 of the above-mentioned application Ser. No. 383,950. In each such laser receiver arrangement, a small laser 180, such as a continuous wave laser diode of the GOLS series made by General Optronics of South Plainfield, N.J., is mounted in the center of an array 182 of photo diodes to project a beam 184 through a central aperture of a lens 186. Each combination of laser, photo diode array, and lens is mounted near the outer periphery of the rotating scanner disc 156 that itself is mounted for rotation about the axis of motor shaft 152. Suitable electrical leads (not shown) are carried through the slip rings to provide power to the laser and to transmit intensity signals from the photo diode array. The arrangement operates for XY reflection intensity data just as the previously described arrangements. Light from the laser is transmitted through the hole in the lens to the surface of a part to be identified. Light reflected from the part is collected by the lens and transmitted to the photo diode detector to provide the desired intensity signals. Use of a larger photo diode detector array provides more information by collating reflected light from a larger area. A Fresnel lens is preferred for use of a larger detector. If the detector is sufficiently large, the assembly of laser and detector may be placed on the rotating disc at a position so close to the object being scanned that no interposed collecting lens need be employed. Each of the assemblies 160, 162, 164 and 166 is identical with the arrangement described and illustrated in FIG. 4, and signals to each of the lasers and from all of the receivers and detectors may be sent out to the data processing equipment via the slip rings. Alternatively, the rotatable disc may carry suitable electronics, generally indicated at 166, and including a multiplexer, so that fewer data channels and fewer power channels need pass through the shaft slip rings.

Also illustrated in the arrangement of FIG. 4 is a plurality of inclined axis elevation receiver assemblies 188, 190, 192 and 194 spaced generally equally about the laser receiver assembly 164. Each of the inclined axis elevation receivers 188, 190, 192 and 194 may be the same as the elevation receiver assembly 110 illustrated in FIG. 3. The use of a plurality of such elevation receivers, each having its axis pointed at and intersecting the axis of the projected laser beam at an expected intermediate or nominal elevation of the object surface, prevents loss of information when the elevation contour of the object is such that certain areas illuminated by the projected laser beam may be hidden from the line of sight of one of the elevation receivers. Thus, elevation information of all sides of a hole or sharp projection may be obtained by use of the illustrated group of elevation receivers, all pointed at the area illuminated by a single scanning beam.

It will be understood that in all of the arrangements described herein the depth of focus of the scanning laser beam, which is nominally focused on the surface of an object at a predetermined nominal elevation, is such that the projected beam is adequately focused upon the object surface within an acceptably large range of elevation variations. Of course, any reasonable number (two, three, or more than four) of the solid-state laser receiver combinations 160, 162, 164 and 166 may be employed and spaced around the periphery of the rotating disc so as to increase the speed of the scan or to increase scan resolution, or both. Similarly, different numbers of inclined axis elevation receiver assemblies may be employed for one or more of such projected beams, as deemed necessary or desirable. Instead of using additional solid-state laser receiver combinations for increased resolution or speed, or merely to provide redundant data, the information from one or more of the receivers may be processed so as to inspect, measure, or analyze different surface characteristics, other than reflection intensity, such as, for example, the angle of the part surface relative to the beam axis. The amount of reflected light at each of a plurality of receivers varies with surface angle, whether the receiver is coaxial with the illuminating beam or displaced therefrom. Thus, relative intensities of reflected light at the several receivers will provide information concerning surface angle.

Figure 6:
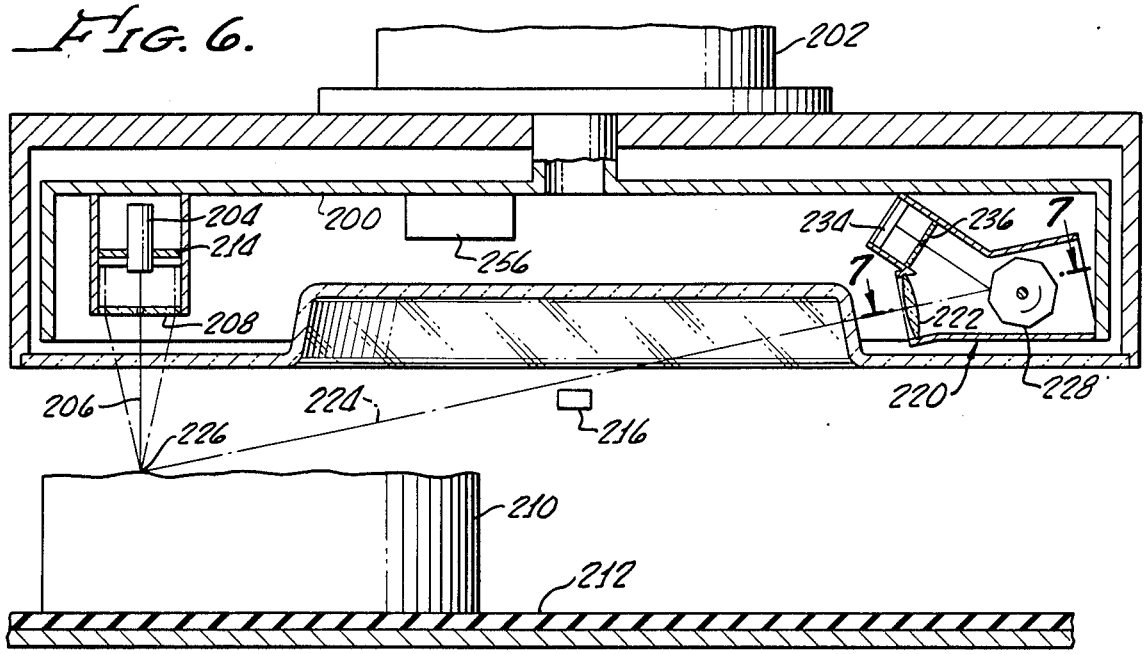
FIGS. 6 and 7 show still another modification of the elevation scanning aparatus of the present invention.

Illustrated in FIG. 6 is a scanning system having a modified elevation scan receiver that operates together with a scanning laser and reflection intensity receiver of the type described above. A scanner support disc 200 is rotated at high speed by a motor 202 and carries a solid-state laser 204 adapted to project an energy beam 206 through the aperture in a receiving lens 208 for reflection from an object 210 carried on a conveyor 212. The axis of beam 206 moves through a right, circular, cylindrical scan and is at all times perpendicular to the direction of motion of the object, as carried by the conveyor, entirely across the scan. Light reflected from the object 210 is collected by receiving lens 208 and focused upon an array of detectors 214 which provides information concerning the illuminated surface areas, such as reflection intensity. One or more reference detectors 216 produce one or more reference pulses for each rotation of disc 200, and a detector or encoder (not shown in FIG. 6), coupled with the conveyor drive, produces pulses representing position of the conveyor and, therefore, the object carried on the conveyor in the direction of travel of the conveyor. The signals from detectors 216 and 218 are sampled or clocked at a very high repetition rate to thereby provide a set of electrical signals that collectively define the coordinate position of the axis of beam 206 in a plane fixed relative to the object 210 and normal to the beam axis 206 at each of a large number of closely spaced points on the object surface. The structure described to this point is the same as the corresponding structure illustrated and described in connection with FIGS. 4 and 5.

Figure 7:
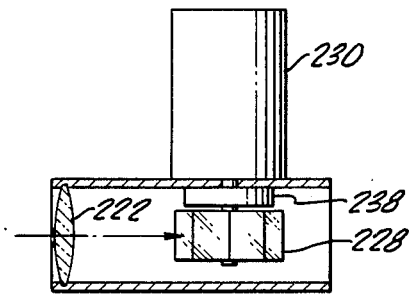

In the arrangement of FIGS. 6 and 7, a second or elevated receiver 220 is fixedly mounted to the rotating disc 200 for rotation therewith. The elevation receiver includes a receiver lens 222 having its axis 224 directed to intersect the beam axis 206 at a point 226 positioned along the beam axis 206 intermediate expected extremes of surface elevation of the object 210. Lens 222 directs received light to the surface of a polygonal mirror 228 that is rotatably mounted to the disc 200 adjacent the lens and rotatably driven by a motor 230 (FIG. 7) also carried by the disc 200. Light reflected from illuminated areas on the surface of object 210 is collected by lens 222 and directed to the several surfaces of mirror 228, one after the other, as the mirror rotates. Light reflected from the several surfaces of the mirror is directed toward a light detector 234 through an optical slit 236. A shaft position encoder 238 (FIG. 7) provides a series of output pulses that indicate angular position of the rotating mirror 228. The output of detector 234 has a peak magnitude when each reflective surface of the mirror attains a position, in the course of its angular rotation, in which it will reflect light through the optical slit 236. The angular position of the rotating mirror 228 at the time of occurrence of the peak output on detector 234 is a measure of the relative elevation of the illuminated spot 226 of the object 210.

Figure 8:
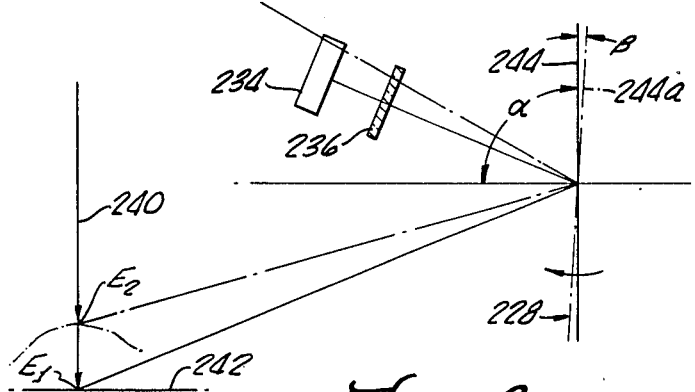
FIG. 8 depicts geometry useful in understanding the operation of the arrangement of FIG. 2.

The operation of the elevation detection arrangement of FIG. 6 may be understood in connection with the simplified geometry illustrated in FIG. 8. Assume that a scanning beam 240 strikes the surface of an object 242 at a point $E_1$. Assume also that, with a surface 244 of the mirror 228 angularly positioned at an angle $\alpha$ with respect to a perpendicular to the axis of beam 240, light is reflected from point $E_1$ through the optical slit 236 for maximum reception by detector 234. At other angular positions of the mirror surface 244, light reflected from point $E_1$ will be displaced to one side or the other of the optical slit, whereby the amount of light received by detector 234 is diminished.

Consider now the object to have a different elevation, so that the axis of beam 240 strikes the surface at a point indicated at $E_2$, which is at an elevation higher than (closer to the rotating disc) than point $E_1$. If the mirror surface 244 is rotated through the angle $\beta$ from its position at angle $\alpha$ to a position 244a, light reflected from point $E_2$ will be directed through the optical slit 236, whereas light reflected from a point at a lower elevation, such as $E_1$, now will be reflected from the mirror surface in position 244a to one side of the optical slit. Thus, for a point at elevation $E_2$, the peak intensity of the output of detector 234 occurs with the mirror in the angular position $\alpha+\beta$. Accordingly, it will be seen that the elevation difference between $E_2$ and $E_1$ is a readily identifiable function of the angular position of the mirror surface at the time of occurrence of the peak output of detector 234. For very small elevations the distance between $E_2$ and $E_1$ is substantially equal to one half tangent $\beta$.

Figure 9:
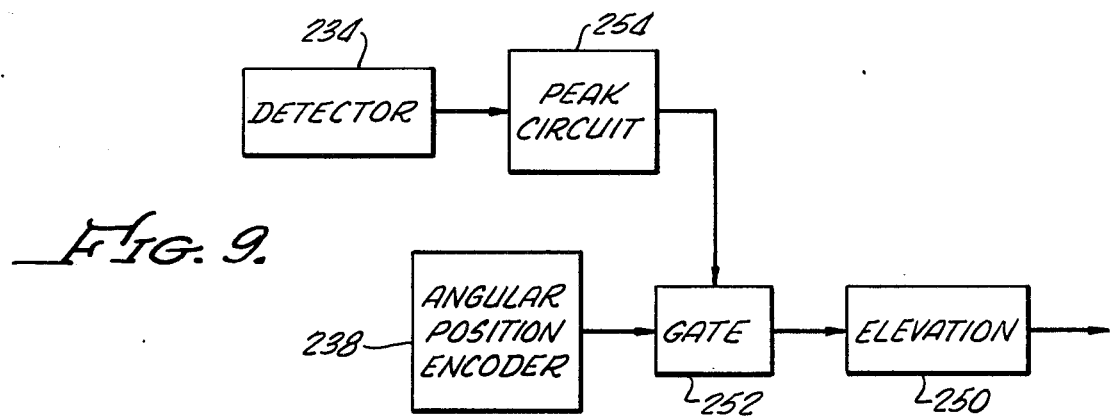
FIG. 9 is a block diagram of certain circuits for the modification of FIGS. 6 and 7.

Thus, as functionally illustrated in FIG. 9, the angular position of mirror 228, as sensed by the rotational position encoder 238, is fed to an elevation circuit 250 via a gate 252 which is enabled by a peak detecting circuit 254 connected to receive the output of detector 234. Power for laser 204 and motor 230, and signals from detectors 214, 234 and 238 may be processed and distributed by means of circuitry 256 carried by the rotating disc. The signals are communicated to external circuitry for display and computation via motor shaft slip rings (not shown in FIG. 6).

The foregoing detailed description is to be clearly understood as given by way of illustration and example only, the spirit and scope of this invention being limited solely by the appended claims.

What is claimed is:

1. Scanning apparatus comprising
   a movably mounted support,
   means for projecting an energy beam from said support along a beam axis directed to an object to be scanned,
   means for effecting relative scanning motion of said support and an object to be scanned whereby said beam scans across the object in a scan pattern,
   first and second mutually spaced energy receivers mounted to said support for motion therewith relative to the object to be scanned, means for moving the object relatively to the scan pattern,
   said beam illuminating areas of said object in said scan pattern, one of said receivers having an energy receiving axis inclined to the beam axis and directed at said illuminated areas, and means for generating signals that define position of said illuminated areas in a plane parallel to the direction of motion of the object relative to the scan pattern.

2. Apparatus according to claim 1 wherein said one receiver includes means for generating signals representing elevations of said illuminated areas relative to said plane.

3. Scanning apparatus comprising
   a movably mounted support,
   means for projecting an energy beam from said support along a beam axis directed to an object to be scanned,
   means for effecting relative scanning motion of said support and an object to be scanned whereby said beam scans across the object in a scan pattern,
   first and second mutually spaced energy receivers mounted to said support for motion therewith relative to the object to be scanned, means for moving the object relatively to the scan pattern,
   said means for effecting relative scanning motion comprising means for mounting the support for rotation about an axis perpendicular to the direction of motion of the object relative to the scan pattern, a detector, said first receiver comprising means for transmitting to said detector an image of an area of said object illuminated by said beam and reflected at an angle to said beam axis.

4. Scanning apparatus comprising
   a movably mounted support,
   means for projecting an energy beam from said support along a beam axis directed to an object to be scanned,
   means for effecting relative scanning motion of said support and an object to be scanned whereby said beam scans across the object in a scan pattern,
   first and second mutually spaced energy receivers mounted to said support for motion therewith relative to the object to be scanned, means for moving the object relatively to the scan pattern, and
   second means for projecting a second energy beam from said support along a second beam axis directed to said object, whereby said second energy beam scans across the object in a scan pattern, said first and second receivers each having a receiving axis directed to receive energy of respective ones of said beams as reflected from said object, whereby said object may be scanned by two beams.

5. The apparatus of claim 4 wherein at least one of said means for projecting an energy beam comprises a laser mounted on said support for motion therewith, at least one of said receivers having its receiving axis coaxial with the axis of one of said beams.

6. The apparatus of claim 4 wherein said means for effecting relative scanning motion comprises means for mounting said support for rotation about an axis parallel to said beam axis of said first mentioned beam, said second beam having an axis parallel to said first beam axis.

7. The apparatus of claim 3 wherein said second receiver has a receiving axis coaxial with said beam axis, and including a second detector positioned to receive energy of said beam reflected from said object and collected by said second receiver.

8. The apparatus of claim 3 wherein said first receiver comprises an optical slit mounted adjacent said detector, a mirror position to reflect said image toward said slit, means for mounting said mirror to said support for rotation relative to said support, means for rotatably driving said mirror to shift said image across said slit, whereby said image will pass through said slit to said detector in the course of rotation of the mirror, and means for indicating the angular position of said mirror to indicate position of said area along said beam axis.

9. Scanning apparatus comprising
   a movably mounted support,
   means for projecting an energy beam from said support along a beam axis directed to an object to be scanned,
   means for effecting relative scanning motion of said support and an object to be scanned whereby said beam scans across the object in a scan pattern,
   first and second mutually spaced energy receivers mounted to said support for motion therewith relative to the object to be scanned, and means for moving the object relatively to the scan pattern,
   said beam illuminating areas of said object in said scan pattern, and one of said receivers being offset from said projected beam axis adjacent said illuminated areas.

10. Scanning apparatus comprising
    a movably mounted support, means for projecting an energy beam from said support along a beam axis directed to an object to be scanned, means for effecting relative scanning motion of said support and an object to be scanned whereby said beam scans across the object in a scan pattern, first and second mutually spaced energy receivers mounted to said support for motion therewith relative to the object to be scanned, and means for moving the object relatively to the scan pattern, said beam axis being substantially normal to the direction of motion of the object relative to the pattern, and said first receiver, having an energy receiving axis inclined to the beam axis and directed at said illuminated areas.

11. Apparatus according to claim 10 wherein said second receiver has an energy receiving axis coaxial with the beam, said last-mentioned receiving axis having a scanning motion relative to the object to be scanned, whereby said second receiver will receive energy of the beam reflected from the object through an area centered upon the projected beam axis.

12. Apparatus according to claim 10 wherein said first receiver includes a detector and a lens for focusing on said detector an image of an area illuminated by the beam, whereby the position of the image on the detector varies according to the position of the illuminated area along the beam axis.

13. A method of scanning an object comprising projecting an energy beam at the object to cause energy of the beam to be reflected from the object, moving the beam across the object to provide an illuminated area that traverses the object in a scan pattern, positioning first and second reflected energy receivers to receive energy reflected along first and second receiver axes, moving said receivers in synchronism with said beam to cause the receiver axes to scan the object in said scan pattern, relatively moving said object and scan pattern, and generating signals defining positions of said illuminated area in a plane parallel to the direction of motion of said object and scan pattern.

14. The method of claim 13 including the step of directing the axis of said first receiver toward said illuminated area in a direction inclined to the axis of the projected beam, and employing energy received by said first receiver to indicate position of the illuminated area along the axis of the projected beam.

15. The method of claim 13 including the step of directing both said receiver axes to intersect said energy beam.

16. A method of three dimensional scanning of an object comprising moving a scanning energy beam in a scan pattern across the object to successively illuminate small areas of the object, generating position signals defining position in a plane of a plurality of said illuminated areas, moving a scanning receiver across the object in synchronism with the energy beam to receive energy reflected from said illuminated areas at an angle to a normal to said plane, and generating, from reflected energy received by the receiver, elevation signals defining relative elevations of said illuminated areas.

17. The method of claim 16 including the step of moving a second scanning receiver across the object in synchronism with the energy beam to receive energy reflected from said illuminated areas back along the axis of said scanning energy beam, and generating, from reflected energy received by said second receiver, signals defining intensity of energy reflected from said illuminated areas.

18. Scanning apparatus comprising a support, means for mounting the support for rotation about a rotation axis, means for rotatably driving the support, means carried by the support for projecting an energy beam parallel to said axis in a scan pattern, an object carrier mounted adjacent said support for transporting an object to be scanned across said scan pattern, whereby areas of an object carried by the carrier are successively illuminated by said energy beam, an energy receiver mounted to said support for receiving energy reflected from said object at an angle to said axis, and means responsive to said receiver for generating signals defining elevation of said illuminated areas in a direction parallel to said axis.

19. The scanning apparatus of claim 18 including a second energy receiver mounted to said support for receiving energy reflected from said object back along said projected beam, mans responsive to said second receiver for generating signals indicating intensity of energy reflected from said illuminated areas, and means for generating position signals defining positions of said illuminated areas in a plane normal to said axis.

20. The scanning apparatus of claim 18 wherein said first mentioned energy receiver comprises a detector array on said support and a lens on the support for focussing on the detector images of said illuminated areas.

21. The apparatus of claim 18 wherein said means for projecting an energy beam comprises a laser mounted on said support for rotation therewith, and a second energy receiver mounted to said support for receiving energy reflected from said object, both said receivers having receiving axes directed to intersect said energy beam, and means for generating signals defining positions of said illuminated areas in a plane normal to said axis.

22. Elevation scanning apparatus comprising a support, a mirror rotatably mounted on the support, means for rotating the mirror, a lens for collecting light from a point of which elevation is to be determined and for directing collected light to a surface of the mirror, a detector for receiving light collected by the lens and reflected by the mirror, an optical slit interposed between the detector and mirror, peak detecting means coupled with said detector, and means responsive to said peak detecting means for indicating angular position of the mirror upon occurrence of a peak output from the detector.

23. The elevation apparatus of claim 22 including means for rotatably mounting said support, means for rotatably driving the support, and means on the support for projecting a scanning beam at an object in a scan pattern that repetitively traverses the object, said lens being positioned on the support to collect light reflected from areas on an object illuminated by said beam.

24. The elevation apparatus of claim 23 including means for transporting an object across the scan pattern of the projected beam, and means for generating signals collectively defining positions of areas of the object successively illuminated by the projected beam.

25. The apparatus of claim 23 including receiver means on said support for collecting light reflected back along the axis of said scanning beam from said illuminated areas.

* * * * *

UNITED STATES PATENT AND TRADEMARK OFFICE
CERTIFICATE OF CORRECTION

PATENT NO. : 4,622,462

DATED : November 11, 1986

INVENTOR(S) : Homer L. Eaton and John D. Shaylor-Billings

It is certified that error appears in the above-identified patent and that said Letters Patent is hereby corrected as shown below:

Claim 19 (column 12, line 30), delete "mans" and insert —means—.

Signed and Sealed this

Seventh Day of April, 1987

Attest:

DONALD J. QUIGG

Attesting Officer

Commissioner of Patents and Trademarks